United States Patent [19]

Goel

[11] Patent Number: 4,661,600

[45] Date of Patent: Apr. 28, 1987

[54] MANUFACTURE OF 2-OXAZOLINES, 2-OXAZINES, 2-IMIDAZOLINES AND 2-IMIDAZINES

[75] Inventor: Anil B. Goel, Worthington, Ohio

[73] Assignee: Ashland Oil, Inc., Ashland, Ky.

[21] Appl. No.: 736,172

[22] Filed: May 20, 1985

[51] Int. Cl.$^4$ .................. C07D 498/04; C07D 233/04
[52] U.S. Cl. ..................................... 548/217; 544/88; 544/242; 548/218; 548/219; 548/239; 548/347; 548/353
[58] Field of Search ............... 548/217, 218, 219, 353, 548/347, 239; 544/88, 242

[56] References Cited

U.S. PATENT DOCUMENTS

| | | | |
|---|---|---|---|
| 2,448,890 | 9/1948 | Johnston | 548/218 |
| 4,501,679 | 2/1985 | Reierson et al. | 548/218 |

FOREIGN PATENT DOCUMENTS

| | | | |
|---|---|---|---|
| 2344607 | 3/1975 | Fed. Rep. of Germany | 548/218 |
| 2512980 | 12/1975 | Fed. Rep. of Germany | 548/218 |
| 2454740 | 5/1976 | Fed. Rep. of Germany | 548/218 |
| 3143251 | 5/1983 | Fed. Rep. of Germany | 548/218 |
| 3235933 | 3/1984 | Fed. Rep. of Germany | 548/218 |
| 1592467 | 6/1970 | France | 548/218 |

OTHER PUBLICATIONS

Burzin, Chem. Abst., 81-25594.
Chemische Werke Huels A-G, Chem. Abst., 75-31744c.

Primary Examiner—Donald G. Daus
Assistant Examiner—Cecilia Shen
Attorney, Agent, or Firm—John F. Jones

[57] ABSTRACT

A process for the production of a product selected from the group consisting of a 2-oxazoline or a 2-oxazine and a 2-imidazoline or a 2-imidazine comprising reacting a bicyclic amide acetal with a member selected from the group consisting of an alkanol amine and an alkylene polyamine, respectively, at a temperature in the range of from about 20° C. to 200° C. is described.

11 Claims, No Drawings

MANUFACTURE OF 2-OXAZOLINES, 2-OXAZINES, 2-IMIDAZOLINES AND 2-IMIDAZINES

This invention relates to a process for the preparing 2-oxazolines or 2-oxazines and 2-imidazolines or 2-imidazines by the reaction of an alkanol amine or an alkylene polyamine, respectively, with a bicyclic amide acetal.

The synthesis of oxazolines and imidazolines is known in the prior art and usually involves high temperature reactions in the order of 200 degrees C. or higher of a carboxylic acid or its ester with an alkanol amine or an alkylene diamine, respectively. The synthesis of oxazolines and imidazolines can also be carried out by the reaction of alkyl or aryl nitriles with alkanol amines or alkylene diamines, respectively according to the prior art. Although the synthesis of oxazolines from nitriles is reasonably fast, the unavailability of some nitriles makes this method of synthesis somewhat unattractive. The synthesis of oxazolines and imidazolines by reaction of bicyclic amide acetals with alkanol amines or alkylene polyamines, respectively, has not previously been reported.

Bicyclic amide acetals are described in Angew Chem. 85, (1973), in German Patent Publication No. 2,344,607, in *Synthesis*, pp. 16–26 (1971) and in copending U.S. patent application Ser. No. 641,242, filed 8/16/84.

The compounds resulting from the process of this invention are those having the Formula I $$\left[ (RR'C)_n \begin{array}{c} Y \\ | \\ C \\ | \\ N \end{array} R'' \right]_m \qquad I$$

wherein R and R' are independently hydrogen, an alkyl group having from 1 to 10 carbon atoms, or an aryl group having from 6 to 12 carbon atoms, R'' represents an alkyl group having from 1 to 20 carbon atoms, an aryl group having from 6 to 12 carbon atoms, an alkylene group having from 1 to 19 carbon atoms or an arylene group having from 6 to 12 carbon atoms, n represents 2 or 3, m represents 1 or 2, and Y represents O, S or NR''' wherein R''' represents hydrogen, an alkyl group having from 1 to 10 carbon atoms, an hydroxy alkyl group or an amino alkyl group having from 1 to 10 carbon atoms.

I have found that bicyclic amide acetals of Formula II react readily with alkanol amines such as ethanol amine and alkylene polyamines such as ethylene diamine at a temperature in the range of from about 20° C. to 200° C. to give the corresponding 2-oxazoline or 2-imidazoline, respectively, in high yields.

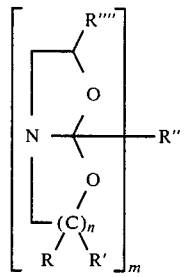

wherein R, R' and R'' n and m have the foregoing designations and R'''' is independently the same as R or R' and may also represent an aliphatic or aromatic ether group having from 1 to 20 carbon atoms.

To illustrate the process of this invention further, the following equation shows in simple form the reaction of essentially equimolar quantities of a bicyclic amide acetal and ethanol amine.

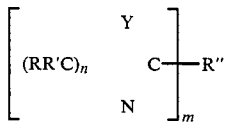 + H₂NCH₂CH₂OH ⟶

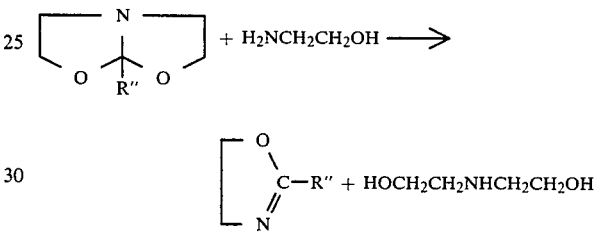

It has been found that monosubstituted bicyclic amide acetals of Formula II in which R, R' and R'''' are hydrogen and R'' is an alkyl, aryl, alkylene or arylene group usually react at a much faster rate with ethanol amine compared with di-, tri- or poly-substituted bicyclic amide acetals. In the reaction illustrated in the equation above wherein R'' in the bicyclic amide acetal represents methyl, which was conducted at 140–160 degrees C., the product (2-methyl-2-oxazoline) was produced in about 80% yield in five minutes.

Alkylene polyamines preferred for use in this invention include ethylene diamine, 1,3-propylene diamine, 1,2-diamino propane 2-(2 amino ethylamino) ethanol and diethylene triamine. Alkanol amines preferred for use in this invention include ethanol amine, propanol amine, 1-amino-2-propanol and 2-amino-2-methyl-1-propanol.

The process of this invention is further illustrated in the following representative examples.

EXAMPLE 1

To a 500 ml three-neck, round-bottom flask equipped with a magnetic stirring bar, a thermometer with a temperature controller, a nitrogen inlet and a distillation head with a condenser and a receiving flask, was added 130 g of methyl substituted bicyclic amide acetal of Formula II in which R, R' and R'''' are hydrogen, R'' is methyl, n is 2 and m is 1, and 30 g of ethanol amine. The reaction mixture was stirred and heated at 140–160 degrees C. under a nitrogen atmosphere. The refluxing of 2-methyl-2-oxazoline was noticed within five minutes. The GLC analysis of the mixture showed almost complete disappearance of ethanolamine and formation of methyl oxazoline. Methyl oxazoline (28 g) was recovered by distillation as a clear, colorless liquid in approximately 98% purity.

EXAMPLE 2

The procedure of Example 1 was followed using 130 g of the bicyclic amide acetal of Example 1 and 30 g of 1-amino-2-propanol. The resulting mixture was heated at 160–165 degrees C. for 15 minutes. GLC analysis showed the formation of 2,5-dimethyl-2-oxazoline (about 90% based on starting alkanol amine). The product was purified by distillation to give 28 g of colorless mobile oxazoline of about 98% purity.

EXAMPLE 3

The procedure of Example 1 was followed using 100 g of the bicyclic amide acetal of Example 1 and 32 g of 2-amino-2-methyl-1-propanol. GLC analysis of the reaction mixture showed the formation of 2,4,4-trimethyl oxazoline (about 85%) in about 30 minutes of heating at 160 degrees C. The oxazoline product was isolated by distillation (24 g) and was found to be a colorless liquid 98% pure.

EXAMPLE 4

The procedure of Example 1 was followed using 65 g of the bicyclic amide acetal of Example 1 and 30 g of ethylene diamine. The resulting mixture was heated at 110–130 degrees C. for 15 minutes. GLC analysis of the mixture indicated the formation of 2-methyl-2-imidazoline (89%). The product was isolated by sublimation as a white needle-shaped crystalline solid.

EXAMPLE 5

The procedure of Example 1 was followed using 25 g of bicyclic amide acetal having the formula

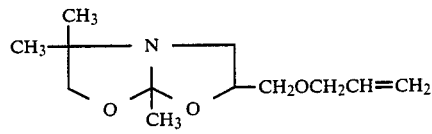

and 6 g of ethanolamine. The reaction mixture was heated at 160 degrees C. for one hour. The GLC analysis of the reaction mixture showed the formation of 2-methyl-2-oxazoline (35% yield based on ethanolamine).

EXAMPLE 6

The procedure of Example 1 was followed using 45 g of disubstituted bicyclic amide acetal of the formula

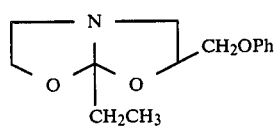

and 10 g of ethanolamine. GLC analysis of the mixture after 15 minutes of heating at 160 degrees C. showed the formation of 2-ethyl-2-oxazoline (90% yield). The product was isolated by distillation and was found to be a colorless liquid of 97% purity.

EXAMPLE 7

The procedure of Example 1 was followed using 65 g of bicyclic amide acetal of Example 1 and 50 g of diethylene triamine. Reaction mixture was heated at about 150° C. for 3 hours during which time almost all the bicyclic amide acetal had reacted to give N-(amino ethyl)-2-imidazoline. This product was allowed to react with excess of acetone at room temperature for 4 hours and analysis by GLC showed that it was converted to N-(dimethylimino ethyl)-2-imidazoline,

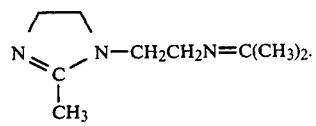

EXAMPLE 8

The procedure of Example 1 was followed using 65 g of the bicyclic amide acetal of Example 1 and 50 g of 2-(2-amino-ethyl amino)ethanol and reaction mixture was heated at 140° C. for about 1 hour. GLC analysis of the mixture showed the complete conversion of bicyclic amide acetal and formation of N-hydroxy ethyl-2-imidazoline,

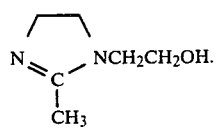

Product was distilled at 115°–25° C./0.1 mm of Hg.

EXAMPLE 9

The procedure of Example 1 was followed using 65 g of the bicyclic amide acetal of Example 1 and 37 g of 1,2-diamino propane. An exothermic reaction occurred and the reaction temperature reached 155° C. GLC analysis indicated that a complete conversion of bicyclic amide acetal occurred within 15 minutes to give 2-methyl-2-imidazine

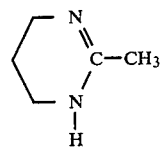

in almost quantitative yield. The product was distilled under vacuum at about 57°–70° C./0.1–0.3 mm of hg in 99% purity.

EXAMPLE 10

A bicyclic amide acetal of Formula I (R=R'=H,R''=Et,—R''''=CH$_2$OCH$_2$CH=CH$_2$) (0.7 g) and ethylene diamine (0.2 g) were mixed in a 5 ml vial and the resulting mixture was heated at about 100° C. for 40 minutes. GLC analysis of the product indicated the formation of 2-ethyl-2-imidazoline in almost quantitative yield.

EXAMPLE 11

The procedure of Example 1 was followed using 35 g of bicyclic amide acetal of Example 1 and 19 g of 3-amino-1-propanol. The reaction mixture upon heating at 130° C. for about 3 hours showed 97% conversion of bicyclic amide acetal and formation of 2-methyl-2-oxazine,

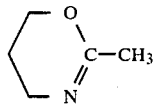

The mixture was subjected to vacuum distillation which afforded 19.2 g of 96% pure oxazine.

I claim:

1. The process for producing a product selected from the group consisting of (A) a 2-oxazoline, (B) a 2-oxazine, (C) a 2 imidazoline and (D) a 2-imidazine comprising reacting a bicyclic amide acetal with a member selected from the group consisting of (A′) a 1,2-alkanolamine, (B′) a 1,3-alkanolamine, (C′) a 1,2-alkylene diamine and (D′) a 1,3-alkylene diamine, respectively, at a temperature in the range of from about 20° C. to 200° C.

2. The process of claim 1 wherein the bicyclic amide acetal is one having the formula:

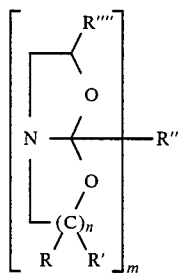

wherein R, R′ and R′′′′ independently represent hydrogen, an alkyl group having from 1 to 10 carbon atoms, or an aryl group having from 6 to 12 carbon atoms, R′′′′ may also represent an aliphatic or aromatic ether group having from 1 to 20 carbon atoms, R′′ represents an alkyl group having from 1 to 20 carbon atoms, an aryl group having from 6 to 12 carbon atoms, an alkylene group having from 1 to 19 carbon atoms, an arylene group having from 6–12 carbon atoms, an alkaryl group or an aralkylene group having from 7 to 15 carbon atoms, n represents 2 or 3 and m represents 1 or 2.

3. The process of claim 1 wherein the alkanol amine is one selected from the group consisting of ethanol amine, propanol amine, 1-amino-2-propanol, 2-amino-2-methyl-1-propanol and the alkylene polyamine is one selected from the group consisting of ethylene diamine, 1,3-propylene diamine, 1,2-diaminopropane, 2-(2-aminoethylamino) ethanol and diethylene triamine.

4. The process of claim 3 wherein the bicyclic amide acetal is one having the formula

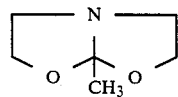

and the alkanol amine is ethanol amine.

5. The procedure of claim 3 wherein the bicyclic amide acetal is one having the formula

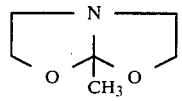

and the alkanol amine is 1-amino-2-propanol.

6. The process of claim 3 wherein the bicyclic amide acetal is one having the formula

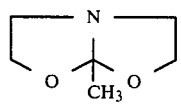

and the alkanol amine is 2-amino-2-methyl-1-propanol.

7. The process of claim 3 wherein the bicyclic amide acetal is one having the formula

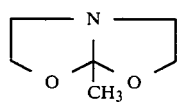

and the alkylene diamine is ethylene diamine.

8. The process of claim 3 wherein the bicyclic amide acetal is one having the formula

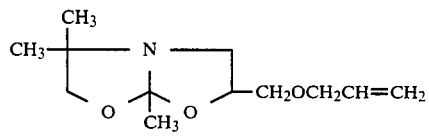

and the alkanol amine is ethanol amine.

9. The process of claim 3 wherein the bicyclic amide acetal is one having the formula

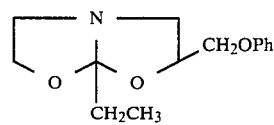

and the alkanol amine is ethanol amine.

10. The process of claim 3 wherein the bicyclic amide acetal is one having the formula

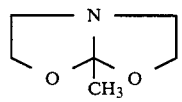

and the alkylene polyamine is diethylene triamine.

11. The process of claim 3 wherein the bicyclic amide acetal is one having the formula

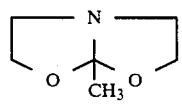

and the alkylene polyamine is 2-(2-amino ethylamino)ethanol.

* * * * *